(12) United States Patent
Hruska et al.

(10) Patent No.: US 8,277,482 B2
(45) Date of Patent: Oct. 2, 2012

(54) CLOSURE DEVICE WITH STRING RETRACTABLE UMBRELLA AND METHOD FOR CLOSING A BODY OPENING WITH THE SAME

(75) Inventors: Christopher L. Hruska, Indianapolis, IN (US); Michael W. Hardert, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/221,337

(22) Filed: Aug. 30, 2011

(65) Prior Publication Data

US 2011/0313451 A1    Dec. 22, 2011

Related U.S. Application Data

(62) Division of application No. 12/404,652, filed on Mar. 16, 2009, now Pat. No. 8,029,534.

(51) Int. Cl.
*A61B 17/08* (2006.01)
*A61D 1/00* (2006.01)

(52) U.S. Cl. ...................................... 606/213

(58) Field of Classification Search .................. 606/151, 606/157, 158, 200, 213, 215–218, 232; 623/23.72, 623/2.2

See application file for complete search history.

(56) References Cited

U.S. PATENT DOCUMENTS

| | | | |
|---|---|---|---|
| 3,874,388 A | 4/1975 | King et al. | |
| 4,007,743 A | 2/1977 | Blake | |
| 4,018,229 A | 4/1977 | Komiya | |
| 5,108,420 A | 4/1992 | Marks | |
| 5,171,259 A | 12/1992 | Inoue | |
| 5,192,301 A | 3/1993 | Kamiya et al. | |
| 5,433,727 A | 7/1995 | Sideris | |
| 5,649,950 A | 7/1997 | Bourne et al. | |
| 5,709,707 A | 1/1998 | Lock et al. | |
| 5,853,422 A | 12/1998 | Huebsch et al. | |
| 5,921,993 A | 7/1999 | Yoon | |
| 5,944,738 A | 8/1999 | Amplatz et al. | |
| 6,079,414 A | 6/2000 | Roth | |
| 6,080,182 A | 6/2000 | Shaw et al. | |
| 6,117,159 A | 9/2000 | Huebsch et al. | |
| 6,312,446 B1 | 11/2001 | Huebsch et al. | |
| 6,755,868 B2 | 6/2004 | Rousseau | |
| 6,911,037 B2 | 6/2005 | Gainor et al. | |
| 6,913,614 B2 | 7/2005 | Marino et al. | |
| 7,097,653 B2 | 8/2006 | Freudenthal et al. | |
| 7,122,043 B2 | 10/2006 | Greenhalgh et al. | |
| 7,144,410 B2 | 12/2006 | Marino et al. | |
| 7,175,660 B2 | 2/2007 | Cartledge et al. | |
| 7,192,435 B2 | 3/2007 | Corcoran et al. | |
| 7,288,105 B2 | 10/2007 | Oman et al. | |
| 7,338,514 B2 | 3/2008 | Wahr et al. | |
| 7,377,936 B2 | 5/2008 | Gainor et al. | |
| 7,431,729 B2 | 10/2008 | Chanduszko | |
| 7,479,155 B2 | 1/2009 | Gainor et al. | |
| 2001/0039450 A1 | 11/2001 | Pavcnik et al. | |

(Continued)

*Primary Examiner* — Dianne Dornbusch
(74) *Attorney, Agent, or Firm* — Brinks Hofer Gilson & Lione

(57) ABSTRACT

A method for closing a body opening in a patient is disclosed. The method comprises positioning a delivery catheter within the body opening. The delivery catheter includes a closure device comprising a distal occluding body and a proximal occluding body. The closure device is collapsibly disposed within a distal end of the delivery catheter. The method further includes deploying the closure device from the delivery catheter about the body opening such that a distal frame of the distal occluding body expands to its expanded configuration at a distal end of the body opening and a proximal frame of the proximal occluding body expands to its expanded configuration at an opposing proximal end of the body opening.

15 Claims, 6 Drawing Sheets

U.S. PATENT DOCUMENTS

| | | |
|---|---|---|
| 2003/0195530 A1 | 10/2003 | Thill |
| 2004/0220596 A1 | 11/2004 | Frazier et al. |
| 2005/0065548 A1 | 3/2005 | Marino et al. |
| 2005/0085843 A1 | 4/2005 | Opolski et al. |
| 2005/0273124 A1 | 12/2005 | Chanduszko |
| 2006/0009800 A1 | 1/2006 | Christianson et al. |
| 2007/0010852 A1 | 1/2007 | Blaeser et al. |
| 2007/0016250 A1 | 1/2007 | Blaeser et al. |
| 2007/0027456 A1 | 2/2007 | Gartner et al. |
| 2007/0265642 A1 | 11/2007 | Chanduszko et al. |
| 2008/0086168 A1 | 4/2008 | Cahill |
| 2008/0091235 A1 | 4/2008 | Sirota |
| 2008/0249562 A1 | 10/2008 | Cahill |
| 2009/0076541 A1 | 3/2009 | Chin et al. |

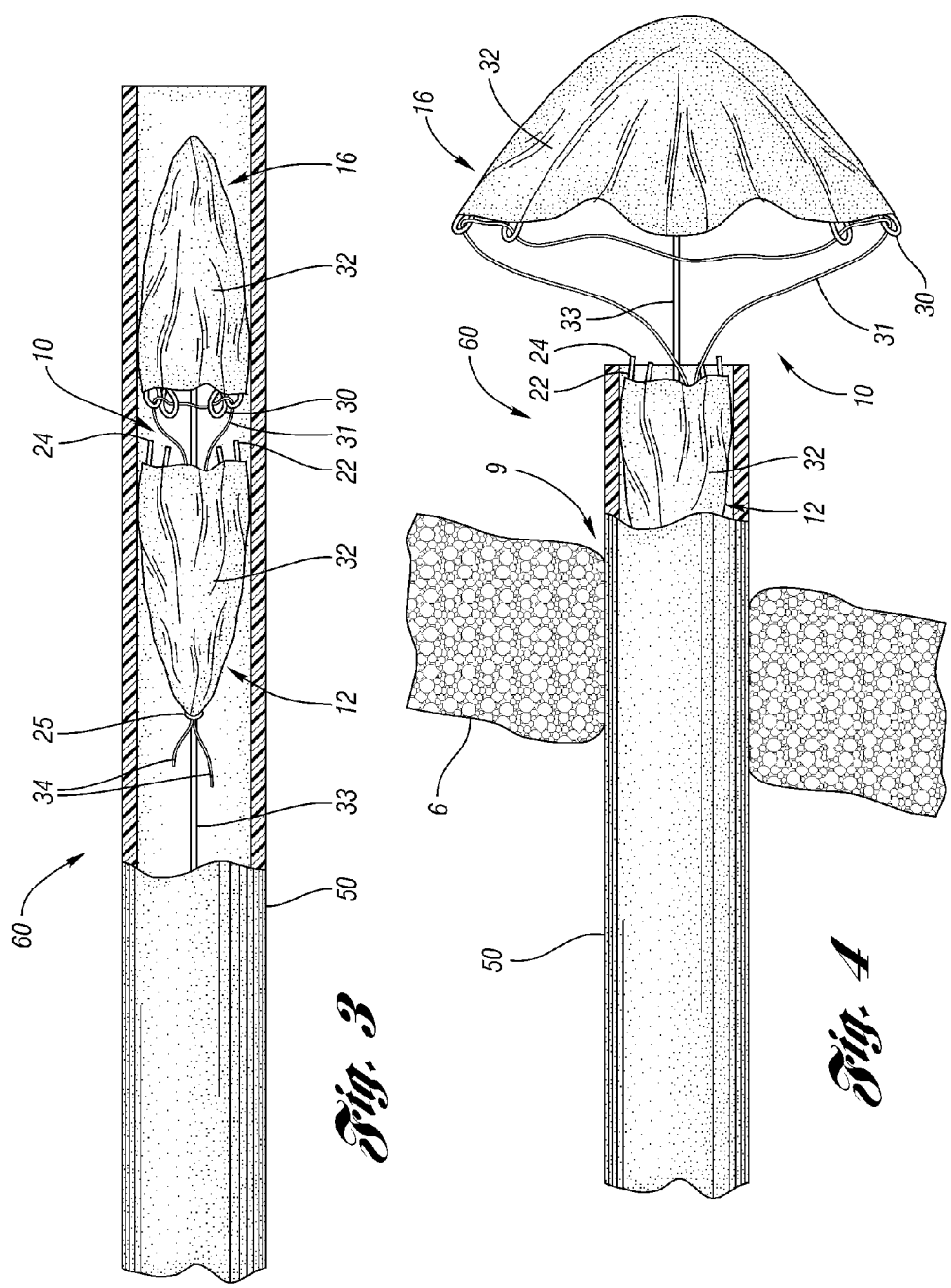

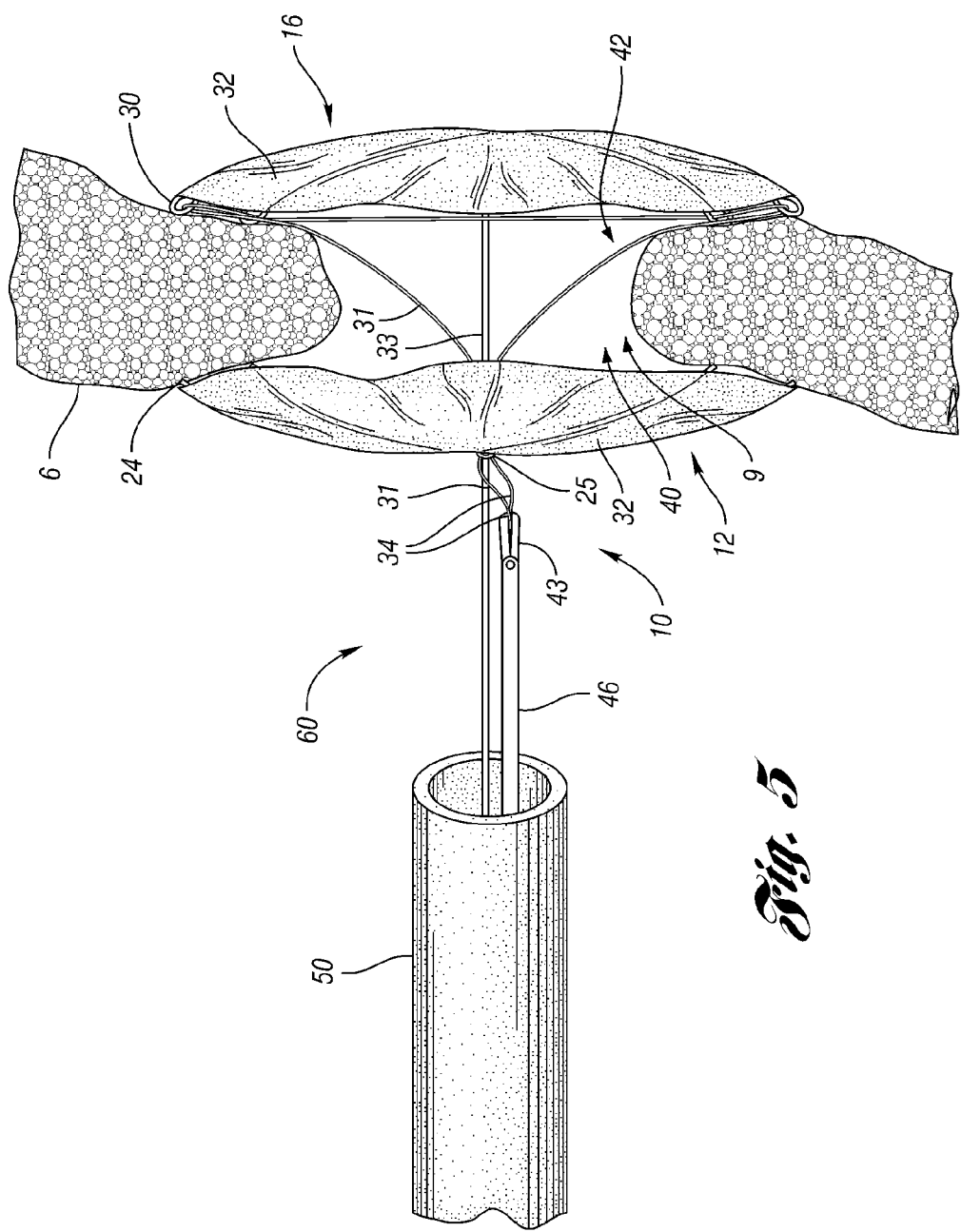

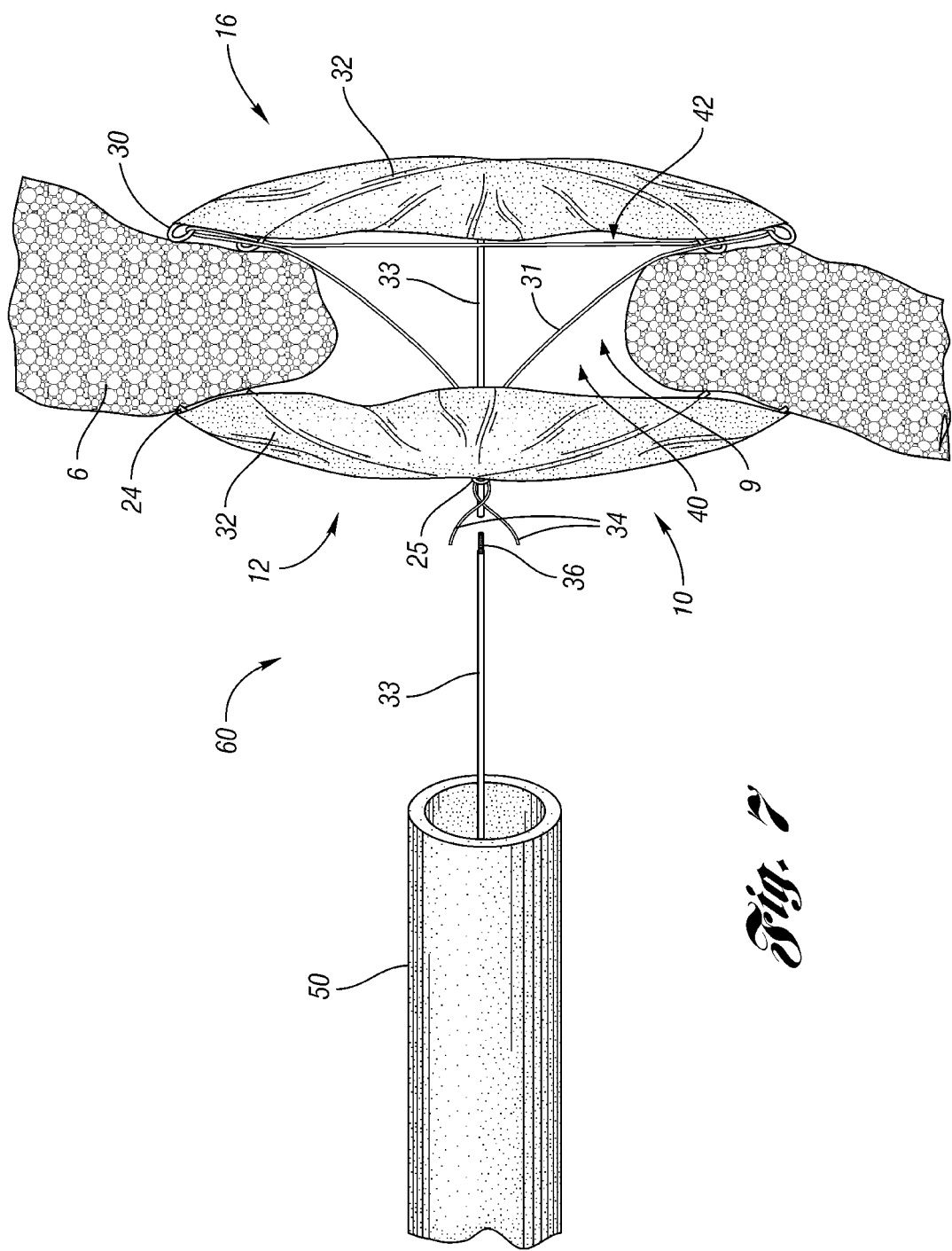

```
┌─────────────────────────────────┐
│  POSITIONING A DELIVERY CATHETER │
│  PROXIMATE A BODY OPENING, THE DELIVERY │──— 100
│  CATHETER INCLUDING A CLOSURE   │
│  DEVICE COLLAPSIBLY DISPOSED WITHIN A │
│  DISTAL END OF THE DELIVERY CATHETER │
└─────────────────────────────────┘
              │
              ▼
┌─────────────────────────────────┐
│      DEPLOYING THE CLOSURE      │──— 102
│      DEVICE ABOUT THE BODY      │
│           OPENING               │
└─────────────────────────────────┘
```

*Fig. 8*

CLOSURE DEVICE WITH STRING RETRACTABLE UMBRELLA AND METHOD FOR CLOSING A BODY OPENING WITH THE SAME

CROSS-REFERENCE TO RELATED APPLICATIONS

This application is a divisional of U.S. patent application Ser. No. 12/404,652, now U.S. Pat. No. 8,029,534, filed Mar. 16, 2009 entitled "CLOSURE DEVICE WITH STRING RETRACTABLE UMBRELLA", which is hereby incorporated by reference in its entirety.

BACKGROUND OF THE INVENTION

1. Field of the Invention

The present invention generally relates to closure devices. More specifically, the invention relates to a closure device for closing physical apertures, such as vascular or septal apertures.

2. Description of Related Art

The heart is generally comprised of four chambers: the left and right atrium and left and right ventricle. Separating the left and right sides of the heart are two walls, or septa. The wall between the two atria is the interatrial septum, and the wall between the two ventricles is the interventricular septum. There are several defects which can affect the septa of both children and adults, including patent ductus arteriosus, patent foramen ovale (PFO), arterial septal defects (ASDs), and ventricular septal defects (VSDs). Although the causes and physical characteristics of these defects vary by type, each of these defects is generally an aperture, flap, or hole in the septum which allows blood to shunt between chambers in the heart where there is no blood flow in a normal, healthy heart. This abnormal shunt can cause a variety of problems.

Normally, permanently repairing certain cardiac defects in adults and children requires open heart surgery, which is a risky, painful, and expensive procedure. Surgery for closure of a heart defect is major heart surgery, which requires the patient to undergo general anesthesia and opening of the chest cavity. The patient must spend several days in the hospital and takes several weeks to be able to return to normal levels of activity.

To avoid the risks and discomfort associated with open heart surgery, modern occlusion or closure devices have been developed that are small, implantable, and capable of being delivered to the heart through a catheter. Rather than surgery, a catheter inserted into a major blood vessel allows an occlusion device to be deployed by moving the device through the catheter to the treatment site within the body. This procedure is performed in a cardiac cathlab and avoids the risks, pain, and long recovery associated with open heart surgery.

There are currently several types of closure devices capable of being inserted via a catheter including button devices, collapsible umbrella-like structures, and plug-like devices. These modem closure devices can repair a wide range of cardiac defects, including patent foramen ovale, patent ductus arteriosus, atrial septal defects, ventricular septal defects, and may occlude other cardiac and non-cardiac apertures. Many of the conventional closure devices can be technically complex, bulky and difficult to deploy in a precise location. In addition, such devices may be difficult or impossible to retrieve and/or reposition should initial positioning not be satisfactory.

SUMMARY OF THE INVENTION

In satisfying the above need, as well as overcoming the enumerated drawbacks and other limitations of the related art, the present invention provides a closure device for occluding a body opening.

In one embodiment, the closure device includes distal and proximal occluding bodies having expandable distal and proximal umbrella frames, respectively. The distal frame is attached at its center to a distal end of a center rod, the distal frame including a plurality of struts having first ends attached to the distal end of the center rod. The proximal frame is slidable along the center rod, which defines a longitudinal axis, via a center ring. The proximal frame includes a plurality of struts having first ends attached to the center ring. The struts of each frame are connected to a biocompatible sheet material which engages the body tissue defining the body opening when the distal and proximal frames are in expanded configurations.

In this embodiment, the distal frame struts extend from the distal end of the center rod in a generally parallel, axial direction with respect to the longitudinal axis when the distal frame is in a collapsed configuration and in a generally perpendicular, radial direction with respect to the longitudinal axis when the distal frame is in the expanded configuration. The proximal frame struts extend from the center ring in a generally parallel, axial direction with respect to the longitudinal axis when the proximal frame is in a collapsed configuration and in a generally perpendicular, radial direction with respect to the longitudinal axis when the proximal frame is in the expanded configuration. The distal and proximal frames expand to their expanded configurations on opposite sides of the body opening.

In this embodiment, each strut of the distal frame extends from the first end and terminates with an eyelet. A drawstring is threaded through the eyelets of the distal frame and through the center ring of the proximal frame to connect the distal and proximal occluding bodies to one another. The drawstring extends proximally from the center ring and manipulation of the center rod and the drawstring is configured to move the distal and proximal frames from their expanded configurations toward their collapsed configurations for at least partial retrieval of the closure device to more optimally position the closure device.

In another embodiment, a first drawstring is threaded through the eyelets of the distal frame and through the center ring of the proximal frame to connect the distal and proximal occluding bodies to one another and a second drawstring extends proximally from the center ring. In this embodiment, manipulation of the center rod and the second drawstring is configured to move the distal and proximal frames from their expanded configurations toward their collapsed configurations for at least partial retrieval of the closure device to more optimally position the closure device.

In another embodiment, a closure device assembly includes a closure device, as described above, collapsibly disposed within the distal end of a delivery catheter. The closure device assembly further includes a grasping instrument for manipulating the drawstring extending proximally from the center ring.

In another embodiment, a method for closing a body opening in a patient comprises positioning a delivery catheter within the body opening, the delivery catheter including a closure device, as described above, collapsibly disposed within the distal end of the delivery catheter. The method further includes deploying the closure device from the delivery catheter about the body opening such that the distal frame of the distal occluding body expands to its expanded configuration at a distal end of the body opening and the proximal frame of the proximal occluding body expands to its expanded configuration at an opposing proximal end of the body opening.

Further objects, features, and advantages of the present invention will become apparent from consideration of the following description and the appended claims when taken in connection with the accompanying drawings.

BRIEF DESCRIPTION OF THE DRAWINGS

FIG. 3 is a side view of a closure device assembly according to an embodiment of the present invention, the closure device shown in a collapsed delivery configuration;

FIG. 4 is a side view of a closure device assembly according to an embodiment of the present invention, the closure device shown in a partially deployed configuration;

FIG. 5 is a side view of a closure device assembly according to an embodiment of the present invention, the closure device shown in a retrievable deployed configuration;

FIG. 7 is a side view of a closure device assembly according to an embodiment of the present invention, the closure device shown in a fully deployed configuration; and FIG. 8 is a flowchart for a method of closing a body opening of a patient.

DETAILED DESCRIPTION

Figure 1:
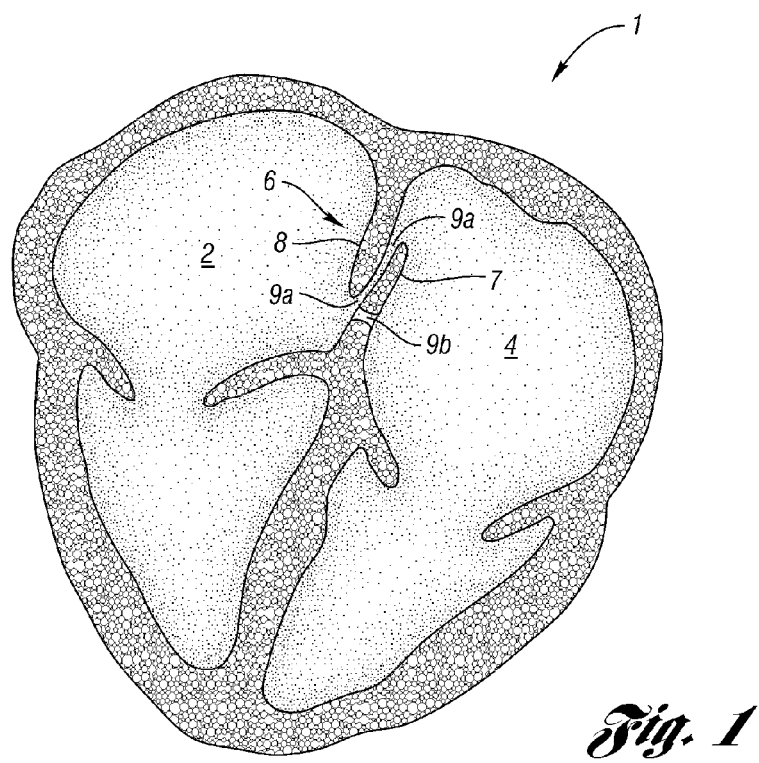
FIG. 1 is a schematic representation of a human heart including various septal defects.

FIG. 1 is a schematic front view of a human heart 1, having a right atrium 2 and a left atrium 4 and including various anatomical anomalies 9a and 9b. The atrial septum 6 between the right atrium 2 and the left atrium 4 comprises a septum primum 7 and a septum secundum 8. The anatomy of the septum 6 varies widely within the population. In some people, the septum primum 7 extends to and overlaps with the septum secundum 8. The septum primum 7 may be quite thin. When anatomical anomalies are present, blood could travel through the opening 9a (referred to as "the PFO tunnel") or 9b (referred to as an "ASD") between septum primum 7 and septum secundum 8.

Figure 2:
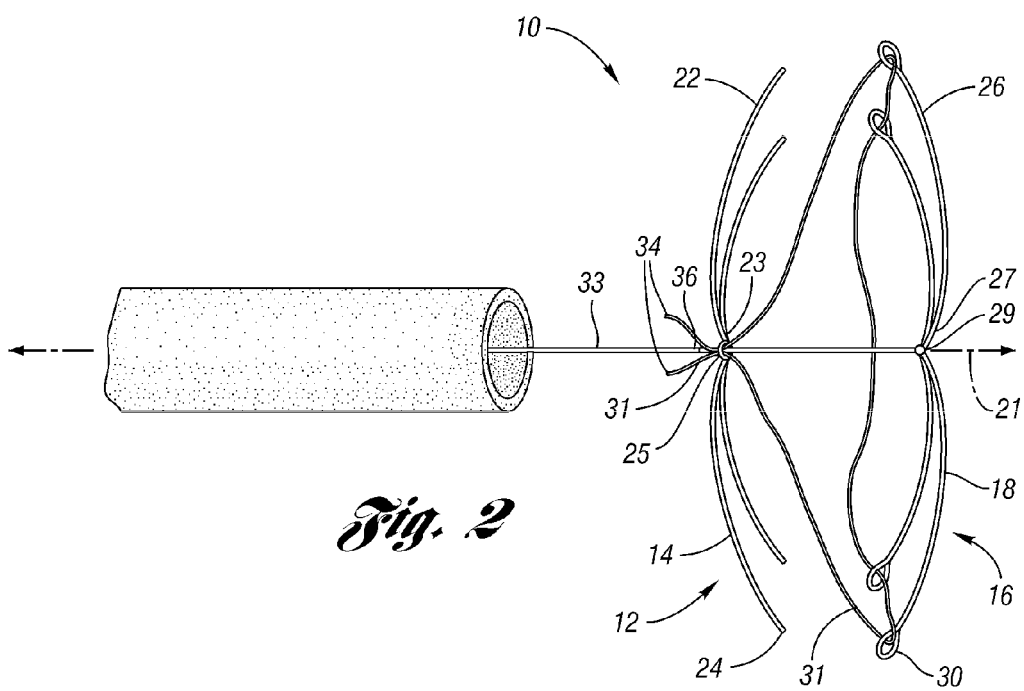
FIG. 2 is a side view of a closure device assembly according to an embodiment of the present invention, the closure device frame shown in an expanded configuration.

Referring to FIG. 2, a closure device embodying the principles of the present invention is illustrated therein and designated at 10. The closure device 10 includes a proximal occluding body 12 formed from an expandable umbrella frame 14 and an opposing distal occluding body 16 formed from an expandable umbrella frame 18. Each of the umbrella frames 14, 18 includes a plurality of struts 22, 26. The struts 22 include first ends 23 attached to a center ring 25, which is slidable along a center rod 33, and the struts 26 include first ends 27 fixedly attached to a distal end 29 of the center rod 33.

In this embodiment, the struts 26 of the distal umbrella frame 18 terminate with eyelets 30 through which at least one suture or drawstring 31 is threaded to form a perimeter about the distal occluding body 16. The drawstring 31 is threaded through, or tied to, the center ring 25 of the proximal umbrella frame 14, forming a loop connecting the proximal occluding body 12 to the distal occluding body 16. Preferably, the drawstring 31 is made of nylon, polyester, or any other suitable material known in the art. The center ring 25 may be made of the same material as the drawstring 31 or the struts 22, 26 (as discussed in more detail below) or any other suitable material in the art.

As illustrated in FIGS. 3-7, the struts 22, 26 of the proximal and distal occluding bodies 12, 16 are connected to or covered by biocompatible or bioremodelable sheet materials 32, which include tissue layers or synthetic polymeric layers formed into a sheet or composite thereof. A sheet of biocompatible or bioremodelable material may include, for example, extracellular matrix tissue, including one or more naturally-derived tissue layers containing an ECM scaffold, one or more biocompatible polymeric layers, or combinations thereof. The sheet of biocompatible or bioremodelable material can be in the form of a single tissue or polymeric layer or a plurality of tissue or polymeric layers in form of laminates, composites, or combinations thereof.

Preferably, the biocompatible sheet materials 32 include bioremodelable sheet materials, such as collagenous ECM materials. Suitable collagenous ECMs include those derived from a variety of native tissues, including but not limited to, intestine, stomach, bladder, liver, fascia, skin, artery, vein, pericardium, pleura, heart valve, dura mater, ligament, tendon, bone, cartilage, bladder, liver, including submucosal tissues therefrom, renal capsule membrane, dermal collagen, serosa, mesenterium, peritoneum, mesothelium, various tissue membranes and basement membrane layers, including liver basement membrane, and the like. Suitable submucosa tissue materials for these purposes include, for instance, intestinal submucosa, including small intestinal submucosa (SIS), stomach submucosa, urinary bladder submucosa, and uterine submucosa. A particularly preferred ECM material is porcine SIS material.

Further examples of biocompatible or bioremodelable sheet materials include thrombogenic fibrous materials, such as (DUPONT, Wilmington, Del., generic name is polyethylene terephthalate), cotton, silk, wool, polyester thread and the like, polyurethanes, and polymeric materials, such as PTFE, ePTFE. Other examples of suitable biocompatible or bioremodelable sheet materials and methods of forming such sheets are described in U.S. patent application Ser. No. 11/845,423, filed Aug. 27, 2007, inventors Kurt J. Tekulve and Dusan Pavcnik, the disclosure of which is expressly incorporated by reference herein.

Biocompatible sheet material 32 may be attached underneath the umbrella frames 14, 18, over the umbrella frames 14, 18, or combinations thereof. The struts 22, 26 may extend through the biocompatible sheet material 32 at one end. Biocompatible or bioremodelable sheet materials 32 may be attached to either side of the struts 22, 26, or both. Biocompatible or bioremodelable sheet materials 32 may be attached to the struts 22, 26 by any suitable attachment method, including but not limited to, use of sutures, chemical cross-linking agents, crimping, tissue welding, heat welding, pressure welding, heat source, light source, radiofrequency, lasering, other energy sources, and the like. Methods for attaching sheet materials to wires or wired frames are described in U.S. Patent Application Publication No. 2001/0039450 A1, the disclosures of which are expressly incorporated by reference herein.

In this embodiment, the umbrella frames 14, 18 are expandable between a collapsed delivery configuration for delivery or at least partial retrieval of the closure device 10 and an expanded configuration for maximizing contact between the biocompatible sheet materials 32 and the body tissue, such as the septum 6, defining a body passageway or opening 9. As used in this application, unless otherwise indicated, the term "body opening 9" refers to any anatomical anomaly or passageway that may be treated by use of the closure device 10, such as a PFO 9a, ASD 9b, VSD (not shown), and/or PDA (not shown).

As depicted in FIG. 2, the struts 22, 26 preferably include an arcuate conformation. In the collapsed delivery configuration, the struts 22 extend from the center ring 25 of the proximal umbrella frame 14 in a generally parallel, axial and distal direction with respect to a longitudinal axis 21 defined by the center rod 33 and the struts 26 extend from the distal end 29 of the center rod 33 in a generally parallel, axial and proximal direction with respect to the longitudinal axis 21. In the expanded deployed configuration, the struts 22 extend from the center ring 25 of the proximal umbrella frame 14 in a generally perpendicular, radial direction with respect to the longitudinal axis 21 and the struts 26 extend from the distal end 29 of the center rod 33 in a generally perpendicular, radial direction with respect to the longitudinal axis 21.

In this embodiment, the arcuate conformation of the struts 22 extending from the first ends 23 to the second ends 24 is defined by a concave surface facing the longitudinal axis 21, and extending in a direction toward the distal occluding body 16 in the collapsed delivery configuration. Similarly, the arcuate conformation of the struts 26 extending from the first ends 27 to the eyelets 30 is defined by a concave surface facing the longitudinal axis 21, and extending in a direction toward the proximal occluding body 12 in the collapsed delivery configuration. The proximal occluding body 12 is configured for placement at a proximal end 40 of the body opening 9 and the distal occluding body 16 is configured for placement at a distal end 42 of the body opening 9, the struts 22, 26 being biased against and engaging the proximal and distal sides of the septum 6, respectively, in the expanded deployed configuration. Thus, as depicted in FIG. 2, the struts 22 are curved in a direction toward the struts 26 and the struts 26 are curved in a direction toward the struts 22 in the expanded deployed configuration. In other words, the struts 22 form a distally facing concave surface and the struts 26 form a proximally facing concave surface in the expanded configuration.

While FIG. 2 depicts each of the proximal and distal umbrella frames 14, 18 of the proximal and distal occluding bodies 12, 16 as having four struts 22, 26, the closure device 10 is not so limited. For example, the closure device 10 may include anywhere between five and ten or more struts on each umbrella frame 14, 18

Preferably, the closure device 10 of the present invention is made of sufficiently flexible materials to facilitate collapsible retention and delivery from a variety of delivery catheter sizes, including 5, 6, 7, or 8 French size delivery catheters having an inner sheath diameter between 0.074 inches and 0.113 inches. The closure device 10 is preloaded at the tip of a delivery catheter in a collapsed, first configuration. When the closure device 10 is expelled from the delivery catheter, it expands to a second, expanded configuration. Accordingly, the closure device 10 is preferably made from flexible and/or shape memory alloy materials, such as Nitinol.

Shape-memory materials, including Nitinol alloys, may be utilized whereby the alloy material(s) is compressed or partially expanded in its martensitic state and fully expanded in its austenitic state. For example, specific shape memory alloy materials may be chosen so that the closure device 10, including the struts 22, 26, is in the austenitic state at body temperature. Prior to insertion into the body, the closure device 10 may be maintained at a low temperature within the martensitic range. Upon delivery to a desired bodily location, the closure device 10 may be warmed to at least the $A_f$ temperature so that, for example, the struts 22, 26 expand to their desired configuration. Preferably, the struts 22, 26 are formed from a superelastic material, stainless steel wire, Nitinol, cobalt-chromium-nickel-molybdenum-iron alloy, or cobalt chrome-alloy, or any other suitable material that will result in a self-opening or self-expanding umbrella frame.

In one embodiment, the umbrella frames 14, 18 may be provided with a radiopaque coating, such as gold or platinum in order to enhance radiopacity so that the frame can be viewed remotely during deployment. Alternatively, radiopaque marker bands may be employed.

FIG. 3 depicts a closure device assembly 60 facilitating deployment of the closure device 10. As illustrated, the closure device assembly 60 includes a delivery catheter 50 containing a preloaded, collapsibly disposed closure device 10 disposed within the lumen of the delivery catheter 50, at the distal end of the delivery catheter 50. In this embodiment, the proximal occluding body 12 is slidable along the center rod 33, via the center ring 25, such that the proximal occluding body 12 is slidable to a position sufficiently proximal from the distal occluding body 16 to prevent the proximal and distal occluding bodies 12, 16 from interfering with one another in their collapsed configurations. Thus, there is a distance along the center rod 33 between the second ends 24 of the struts 22 and the eyelets 30 of the struts 26 in the collapsed delivery configuration.

In this embodiment, the center rod 33 extends proximally from the distal end 29 and through the proximal end of the catheter 50 for manipulation of the center rod 33, and thus the distal occluding body 16, by a physician. Preferably, the drawstring 31 is threaded through, or tied to, the center ring 25 of the proximal umbrella frame 14 such that at least a portion of the drawstring 31 extends proximally from the center ring 25 of the proximal umbrella frame 14. Preferably, the tail ends 34 (i.e., small portions of each end) of the drawstring 31 extend proximally from the center ring 25. The closure device assembly 60 preferably includes a grasping device, such as a bioptome 46, having a grasping portion 43 to grasp the tail ends 34 of the drawstring 31 during delivery and at least partial retrieval of the closure device 10, as illustrated in FIG. 5. The bioptome 46 may be inserted within the delivery catheter 50 to grasp the tail ends 34 after the closure device 10 is positioned within the distal end of the delivery catheter 50.

It is also within the scope of the present invention for the drawstring 31 to extend from the center ring 25 through the proximal end of the delivery catheter 50 such that a physician, rather than a bioptome, may grasp the ends of the drawstring 31 during delivery and at least partial retrieval of the closure device 10. The drawstring 31 connecting the proximal and distal occluding bodies 12, 16 and the drawstring extending through the delivery catheter 50 may be the same drawstring 31, in which case after deployment of the closure device 10 a cutting instrument is used to snip off the drawstring 31 at a point just proximal the center ring 25. Alternatively, the drawstring extending through the delivery catheter 50 may be a separate drawstring than the drawstring 31 connecting the proximal and distal occluding bodies 12, 16, in which case the drawstring extending through the delivery catheter may be looped through the center ring 25 such that removal of the drawstring extending through the delivery catheter 50 merely includes releasing one end of the drawstring and pulling the other end.

FIGS. 4-5 illustrate deployment of the closure device 10. During deployment, the delivery catheter 50, including the closure device 10 in its collapsed delivery configuration disposed within the distal end of the delivery catheter 50, is moved distally through the body opening 9. The distal occluding body 16 is deployed from the distal end of the delivery catheter 50 distally of the septum 6 and the distal end 42 of the body opening 9. The distal occluding body 16 is deployed from the distal end of the delivery catheter 50 by manipulating at least one of the catheter 50 and the center rod 33. For example, a physician may hold the center rod 33 stationary and retract the delivery catheter 50; the physician may hold the delivery catheter 50 stationary and advance the center rod 33; or the physician may retract the delivery catheter 50 and advance the center rod 33 to deploy the distal occluding body 16. As the distal occluding body 16 is released from the constraint of the catheter wall of the delivery catheter 50, it self-expands and retains its original shape, the eyelets 30 of the distal occluding body 16 thus pulling the drawstring 31 to a larger perimeter. As the distal umbrella frame 18 returns to its original shape, it pulls the biocompatible sheet material 32 taut.

Preferably, the bioptome 46 grasps the tail ends 34 of the drawstring 31 to prevent the expanding distal occluding body 16 from pulling the proximal occluding body 16 out of the catheter 50 via the force resulting from the tightening of the drawstring 31 caused by the expansion of the distal occluding body 16. Accordingly, the bioptome 46 grasping the tail ends 34 of the drawstring 31 provides an opposing force which may prevent full expansion of the distal occluding body 16 until the bioptome 46 releases the tail ends 34 of the drawstring 31 and the proximal occluding body 12 is deployed.

Referring to FIG. 5, the delivery catheter 50, including the proximal occluding body 12 in its collapsed delivery configuration disposed within the distal tip of the delivery catheter 50, is retracted through the body opening 9. The center rod 33 is likewise retraced with the delivery catheter 50 through the body opening 9 to move the distal occluding body 16 proximally to engage the septum 6 at the distal end 42 of the body opening 9, and to prevent the proximal occluding body 12 from deploying until positioned at the proximal end 40 of the body opening 9. Likewise, the bioptome 46 preferably holds its grasp of the tail ends 34 of the drawstring 31 until the proximal occluding body 12 is released from the delivery catheter 50. The proximal occluding body 12 is deployed from the distal end of the delivery catheter 50 proximally of the septum 6 and the proximal end 40 of the body opening 9 in the same manner described above with respect to the distal occluding body 16.

In this embodiment, as the proximal occluding body 12 is released from the constraint of the catheter wall of the delivery catheter 50, and the tail ends 34 of the drawstring 31 are released from the grasp of the bioptome 46, the proximal occluding body 12 self-expands and retains its original shape. As the proximal umbrella frame 14 returns to its original shape, it pulls the biocompatible sheet material 32 taut. In this embodiment, the length of the drawstring 31 connecting the proximal and distal occluding bodies 12, 16 is predetermined such that when the distal occluding body 16 expands, there is sufficient force to pull the expanded proximal occluding body 12 distally along the center rod 33 to engage the septum 6 at the proximal end 40 of the body opening 9. The predetermined length of the drawstring 31 is preferably dependent upon the length of the body opening 9 and the distance between the eyelets 30 of the distal umbrella frame 18 in the expanded configuration.

As illustrated in FIG. 7, the center rod 33 is formed from two detachable rod portions, detachable via a screw fit, or any suitable means in the art which allows the center ring 25 to seamlessly slide along the center rod 33. Preferably, the center rod 33 is detachable at a point 36 just proximal the proximal occluding body 12 when in the expanded delivery configuration. Thus, a portion of the center rod 33 remains attached to the distal occluding body 16 and extends just proximally of the proximal occluding body 12 in the expanded configuration.

If the physician is satisfied with the position and sizing of the closure device 10, the detachable portion of the center rod 33 is detached and the detached portion of the center rod 33, the bioptome 46, and the delivery catheter 50 are withdrawn from the patient. If, however, the physician is not satisfied with the position and/or sizing of the closure device 10, or if the closure device 10 has been deployed improperly, the closure device 10 is repositionable.

Figure 6:
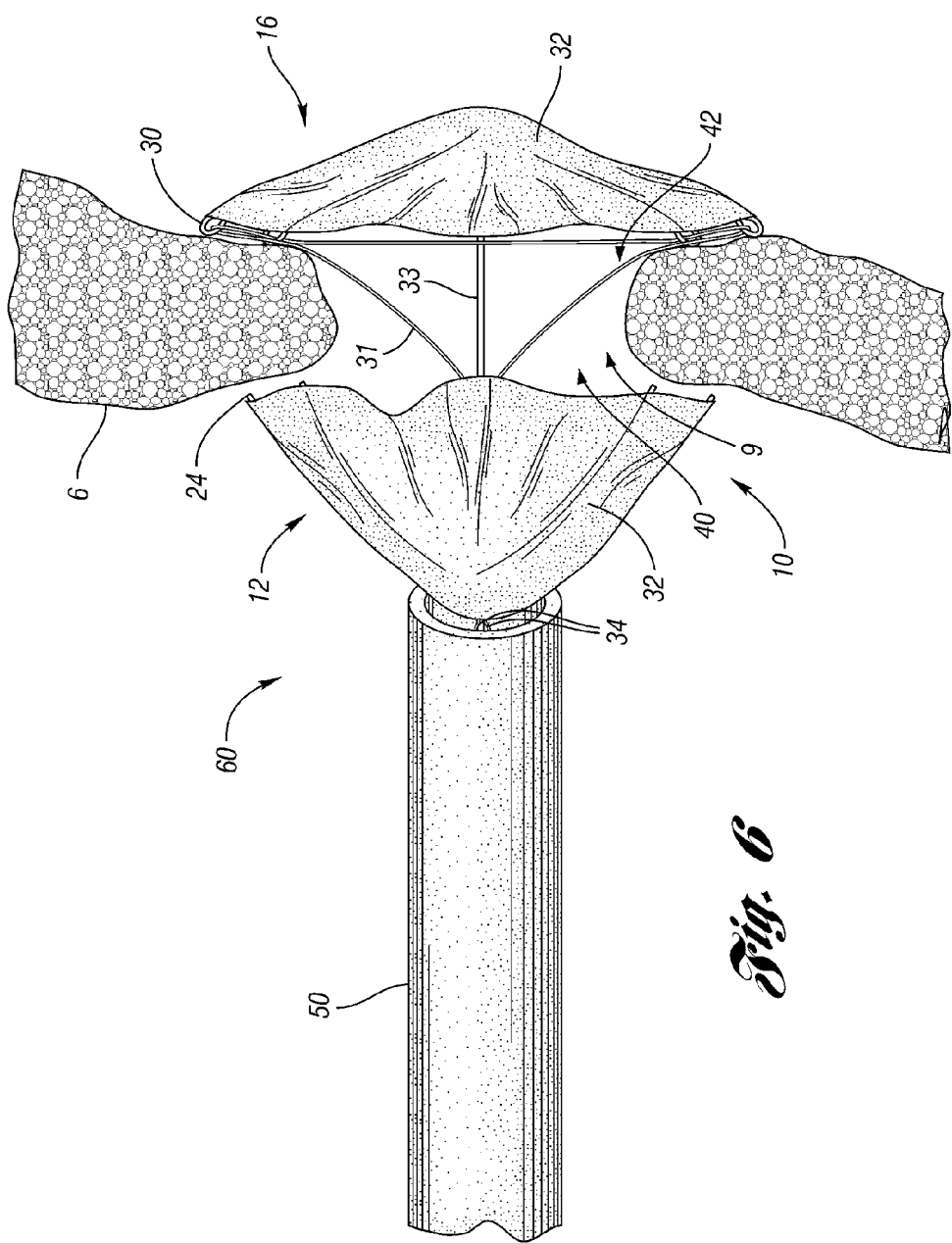
FIG. 6 is a side view of a closure device assembly according to an embodiment of the present invention, the closure device shown in a partially retrieved configuration.

FIG. 6 illustrates the closure device 10 during at least partial retrieval, or repositioning. In this embodiment, the bioptome 46 preferably grasps the tail ends 34 of the drawstring 31 and proximally retracts the drawstring 31 as the center rod 33 is advanced distally. Distally advancing the center rod 33 applies a distal force to the distal occluding body 16 near its center while proximally retracting the drawstring 31 applies an opposing proximal force to the distal occluding body 16 at the eyelets 30 due to the looped drawstring connection between the proximal and distal occluding bodies 12, 16. The combination of the distal and proximal forces on the distal occluding body 16 causes the eyelets 30 of the struts 26 to slide inward along the septum 6 toward the body opening 9.

As the distal occluding body 16 collapses, the bioptome 46 grasping the tail ends 34 of the drawstring 31 is retracted further and the delivery catheter 50 is advanced distally. Further retracting the bioptome 46, and thus the drawstring 31, moves the proximal occluding body 12 proximally and the distal occluding body 16 proximally via the drawstring connection between the proximal and distal occluding bodies 12, 16. Distally advancing the delivery catheter 50 collapses the proximal frame 14 into its collapsed configuration as the catheter 50 receives the proximal occluding body 12. The drawstring 31 is retracted further, pulling the distal occluding body 16 towards the distal end of the delivery catheter 50 and the delivery catheter 50 is advanced to receive the distal occluding body 16, eyelets 30 first. In this embodiment, the physician may redeploy the closure device 10 as described above. Once properly deployed, the physician may detach the center rod 33, remove the bioptome 46 and the center rod 33, and remove the delivery catheter 50 from the patient's body.

In a further aspect, the present invention provides a method for closing or occluding a body opening 9 in a patient using the closure device 10 or closure device assembly 60 as described above. As depicted in the flow chart in FIG. 8, the method comprises positioning (100) a delivery catheter 50 within a body opening 9 of a patient, the delivery catheter 50 including a closure device 10, as described above, disposed within the distal end of the delivery catheter 50 in a collapsed configuration. The method further comprises deploying (102) the closure device 10 from the delivery catheter 50 such that the distal occluding body 16 expands to its expanded configuration and engages the body tissue 6 at the distal end 42 of the body opening 9 and the proximal occluding body 12 expands to its expanded configuration and engages the body tissue 6 at the opposing proximal end 40 of the body opening 9.

Deploying (102) the closure device 10 includes positioning the delivery catheter 50 distal to the distal end 42 of the body opening 9 and moving the delivery catheter 50 and the center rod 33 relative to one another to deploy the distal occluding body 16. Deploying (102) the closure device 10 further includes positioning the delivery catheter 50 proximal to the proximal end 40 of the body opening 9 and moving the delivery catheter 50 and the center rod 33 relative to one another to deploy the proximal occluding body 12.

The method for closing or occluding a body opening 9 may further comprise repositioning the closure device as described above with respect to FIG. 6. After the closure device 10 is properly positioned, the method further includes detaching the detachable portion of the center rod 33 and removing the detached portion of the center rod 33, the bioptome 46, and the delivery catheter 50 from within the patient.

While the present invention has been described in terms of preferred embodiments, it will be understood, of course, that the invention is not limited thereto since modifications may be made to those skilled in the art, particularly in light of the foregoing teachings.

We claim:

1. A method for closing a body opening in a patient comprising:
   positioning a delivery catheter having a proximal end, a distal end, and a lumen formed through the proximal and distal ends within the body opening, the delivery catheter including a closure device collapsibly disposed within the lumen at the distal end of the delivery catheter, the closure device including a distal occluding body having an expandable distal umbrella frame and a proximal occluding body having an expandable proximal umbrella frame, the distal frame including a plurality of struts having first ends attached to a distal end of a center rod, the proximal frame including a center ring and a plurality of struts having first ends attached to the center ring, the center ring being slidable along the center rod, the struts of each frame being connected to a biocompatible sheet material, the center rod defining a longitudinal axis, the distal frame struts extending from the distal end of the center rod in a generally parallel, axial direction with respect to the longitudinal axis when the distal frame is in a collapsed configuration and in a generally perpendicular, radial direction with respect to the longitudinal axis when the distal frame is in an expanded configuration, the proximal frame struts extending from the center ring in a generally parallel, axial direction with respect to the longitudinal axis when the proximal frame is in a collapsed configuration and in a generally perpendicular, radial direction with respect to the longitudinal axis when the proximal frame is in an expanded configuration, each strut of the distal frame extending from the first end and terminating with an eyelet, the closure device further including at least one drawstring threaded through the eyelets of the distal frame and through the center ring of the proximal frame to connect the distal and proximal occluding bodies to one another, the at least one drawstring extending proximally from the center ring; and
   deploying the closure device from the delivery catheter about the body opening such that the distal frame of the distal occluding body expands to its expanded configuration at a distal end of the body opening and the proximal frame of the proximal occluding body expands to its expanded configuration at an opposing proximal end of the body opening.

2. The method of claim 1, wherein deploying the closure device from the delivery catheter includes:
   positioning the delivery catheter distal to the distal end of the body opening and moving the delivery catheter and the center rod relative to one another to deploy the distal occluding body; and
   positioning the delivery catheter proximal to the proximal end of the body opening and moving the delivery catheter and the center rod relative to one another to deploy the proximal occluding body.

3. The method of claim 2, further comprising repositioning the closure device including:
   distally advancing the center rod and proximally retracting the at least one drawstring extending proximally from the center ring to at least partially retrieve the closure device, wherein distally advancing the center rod applies a distal force to the distal occluding body near a center of the distal occluding body, wherein proximally retracting the at least one drawstring applies an opposing proximal force to the distal occluding body at the eyelets, the combination of the distal and proximal forces on the distal occluding body causing the eyelets of the struts of the distal frame to move inward towards the body opening collapsing the distal frame;
   further retracting the at least one drawstring extending proximally from the center ring and distally advancing the delivery catheter, wherein further retracting the at least one drawstring extending proximally from the center ring moves the proximal occluding body proximally and the distal occluding body proximally via the at least one drawstring connecting the proximal and distal occluding bodies, wherein distally advancing the delivery catheter collapses the proximal frame into its collapsed configuration as the delivery catheter receives the proximal occluding body, wherein the delivery catheter receives the distal occluding body as the at least one drawstring extending proximally from the center ring is retracted further and the delivery catheter is advanced further; and
   redeploying the closure device in a more optimal position within the patient.

4. The method of claim 1, wherein the center rod of the closure device includes a first portion and a detachable second portion, the method further comprising withdrawing the delivery catheter from the patient's body opening including:
   detaching the detachable second portion of the center rod from the first portion at a point proximal to the center ring of the proximal frame when the proximal frame is in its expanded configuration; and
   withdrawing the detachable second portion of the center rod.

5. The method of claim 1 wherein the body opening is an atrial septal defect or a patent foramen ovale.

6. The method of claim 1, wherein the body opening is defined by surrounding body tissue, the distal occluding body being configured for placement outside the body opening to engage body tissue adjacent the distal end of the body opening, the proximal occluding body being configured for placement outside the body opening to engage body tissue adjacent the proximal end of the body opening.

7. The device of claim 6, wherein the struts of the distal and proximal frames comprise an arcuate conformation, the struts of the distal frame being biased in a proximal direction against the body tissue adjacent the distal end of the body opening and the struts of the proximal frame being biased in a distal direction against the body tissue adjacent the proximal end of the body opening when the distal and proximal frames are in their expanded configurations.

8. The method of claim 1, wherein the at least one drawstring includes a single drawstring including a first portion connecting the distal and proximal frames to one another and a second portion extending proximally from the center ring.

9. The method of claim 1, wherein the at least one drawstring includes a first drawstring connecting the distal and proximal frames to one another and a second drawstring extending proximally from the center ring.

10. The method of claim 1, wherein the at least one drawstring extending proximally from the center ring includes tails ends which extend proximally from the center ring, wherein a grasping instrument grasps the tail ends during delivery and at least partial retrieval of the closure device.

11. The method of claim 1, wherein the at least one drawstring extending proximally from the center ring includes first and second ends extending through a delivery catheter, wherein the first and second ends of the at least one drawstring are grasped by a physician during delivery and at least partial retrieval of the closure device.

12. The method of claim 1, wherein the biocompatible sheet material is selected from the group consisting of polyethylene terephthalate, PTFE, ePTFE, polyurethane, cotton, silk, wool, polyester, and extracellular matrix material.

13. The method of claim 1, wherein the struts are formed from a material selected from the group consisting of superelastic material, stainless steel wire, Nitinol, cobalt chrome-alloys, and cobalt-chromium-nickel-molybdenum-iron alloy.

14. The method of claim 1, wherein the at least one drawstring connecting the distal and proximal occluding bodies to one another has a predetermined length such that expansion of the distal frame to its expanded configuration moves the proximal frame distally along the center rod.

15. The method of claim 1, wherein the struts of the distal frame extend from the distal end of the center rod in a direction toward the proximal occluding body and the struts of the proximal frame extend from the center ring in a direction toward the distal occluding body when the distal and proximal frames are in their collapsed configurations.

* * * * *